United States Patent [19]

Kawahara

[11] Patent Number: 5,392,638
[45] Date of Patent: Feb. 28, 1995

[54] BUBBLE DETECTING APPARATUS FOR MEDICAL INFUSION DEVICE

[75] Inventor: Masafumi Kawahara, Yamatokoriyama, Japan

[73] Assignee: Sharp Kabushiki Kaisha, Osaka, Japan

[21] Appl. No.: 373,226

[22] Filed: Jun. 29, 1989

[30] Foreign Application Priority Data

Jul. 4, 1988 [JP] Japan .................. 63-166189

[51] Int. Cl.⁶ .............................. G01N 15/02
[52] U.S. Cl. .................... 73/61.49; 73/865.5
[58] Field of Search ............ 73/61 R, 19.03, 865.5, 73/599; 356/335

[56] References Cited

U.S. PATENT DOCUMENTS

| | | | |
|---|---|---|---|
| 3,153,727 | 10/1964 | Nathan | 356/335 X |
| 3,974,681 | 8/1976 | Namery | 73/19.03 X |
| 4,068,521 | 1/1978 | Cosentino et al. | 73/19.03 |
| 4,658,244 | 4/1987 | Meijer | 73/861.04 X |
| 4,763,525 | 8/1988 | Cobb | 73/61 R X |

FOREIGN PATENT DOCUMENTS

| | | |
|---|---|---|
| 56-152652 | 11/1981 | Japan . |
| 57-119758 | 7/1982 | Japan . |
| 60-55960 | 4/1985 | Japan . |
| 62-268565 | 11/1987 | Japan . |
| 658444 | 4/1979 | U.S.S.R. ............. 73/865.5 |

Primary Examiner—Hezron E. Williams
Assistant Examiner—Joseph W. Roskos

[57] ABSTRACT

A bubble detecting apparatus for an infusion pump, including a set of ultrasonic sensor constituted by an ultrasonic oscillator and a receiver provided, respectively, at opposed locations on an outer face of a liquid transport tube for feeding liquid such as medicinal liquid by a predetermined pumping operation of a pumping mechanism such that air bubbles produced in or mixed into the liquid in the liquid transport tube are detected by the ultrasonic oscillator and the receiver. In the apparatus, at least three sets of the ultrasonic sensors are arranged along the liquid transport tube at different intervals.

6 Claims, 2 Drawing Sheets

BUBBLE DETECTING APPARATUS FOR MEDICAL INFUSION DEVICE

BACKGROUND OF THE INVENTION

The present invention relates to a bubble detecting apparatus for detecting air bubbles produced in or mixed into a liquid transport tube for use in a medical infusion device for mainly infusing medicinal liquid into a human body, for example, a peristaltic type infusion pump in which the medicinal liquid is intermittently fed by repeating a predetermined liquid feed process.

Generally, in known liquid transport systems employing liquid infusion pumps, a vial is attached to an upper end of a liquid transport tube assembly from an upper portion of which a drip chamber, a check valve and a Y-shaped injection set are sequentially provided. Meanwhile, an infusion pump is mounted on a lower portion of the liquid transport tube assembly and is constituted by a pumping mechanism, an internal pressure sensor and a bubble detecting apparatus. The bubble detecting apparatus detects downwardly flowing air bubbles produced in or mixed into the liquid transport tube. Operation of the pumping mechanism is stopped in response to a bubble detection signal of the bubble detecting apparatus, thereby eliminating such a phenomenon that a human body is set in a dangerous condition through injection of air bubbles into the human body.

As shown in FIG. 1, the known bubble detecting apparatus includes two ultrasonic sensors 1 and 2. The ultrasonic sensor 1 is constituted by an ultrasonic oscillator 1A and a receiver 1B disposed at opposed locations on an outer face of a liquid transport tube 3. Likewise, the ultrasonic sensor 2 is constituted by an ultrasonic oscillator 2A and a receiver 2B disposed at opposed locations on the outer face of the liquid transport tube 3. The ultrasonic sensors 1 and 2 are axially spaced a distance X from each other. When an air bubble 5 produced in or mixed into medicinal liquid 4 in the liquid transport tube 3 flows in between the ultrasonic sensors 1 and 2 as shown, both ultrasonic waves outputted by the ultrasonic oscillators 1A and 2A, respectively are intercepted by the air bubble 5 and therefore, are not received by the receivers 1B and 2B, whereby it is decided that the air bubble 5 exists.

Meanwhile, in the known bubble detecting apparatus, since presence of the air bubble is detected at the time when both ultrasonic waves from the ultrasonic oscillators 1A and 1B are not received by the receivers 1B and 2B, respectively, the air bubble 5 detectable by the known bubble detecting apparatus is so restricted, in size, as to be larger than the distance X between the ultrasonic sensors 1A and 1B. However, this known bubble detecting apparatus cannot be used in the case where the air bubble 5 has a size smaller than the distance X according to service temperature of the infusion pump, kinds of the medicinal liquid, etc. Even if the air bubble 5 is of a quite small size, injection of the air bubble 5 into the human body may set the human body in a dangerous condition and in some cases, destroys life.

SUMMARY OF THE INVENTION

Accordingly, an essential object of the present invention is to provide, with a view to eliminating the above described conventional inconveniences, a bubble detecting apparatus which is capable of detecting air bubbles of a plurality of kinds of sizes as necessary.

In order to accomplish this object of the present invention, a bubble detecting apparatus for an infusion pump according to the present invention includes a set of ultrasonic sensor constituted by an ultrasonic oscillator and a receiver provided, respectively, at opposed locations on an outer face of a liquid transport tube for feeding therethrough liquid such as medicinal liquid by a predetermined pumping operation of a pumping mechanism such that air bubbles produced in or mixed into the liquid in said liquid transport tube are detected by said ultrasonic oscillator and said receiver, the improvement comprising: at least three sets of said ultrasonic sensors which are arranged along said liquid transport tube at different intervals.

If the three ultrasonic sensors are provided and a distance between the first and second ultrasonic sensors is made different from a distance between the second and third ultrasonic sensors, three detection distances for detecting air bubbles, including a distance between the first and third ultrasonic sensors can be set. Therefore, if arbitrary two of the three ultrasonic sensors are selected for detecting air bubbles, a distance between the two ultrasonic sensors is changed and thus, size of the air bubbles to be detected can be changed.

BRIEF DESCRIPTION OF THE DRAWINGS

This object and features of the present invention will become apparent from the following description taken in conjunction with the preferred embodiments thereof with reference to the accompanying drawings, in which.

Before the description of the present invention proceeds, it is to be noted that like parts are designated by like reference numerals throughout the accompanying drawings.

DETAILED DESCRIPTION OF THE INVENTION

Figure 1:
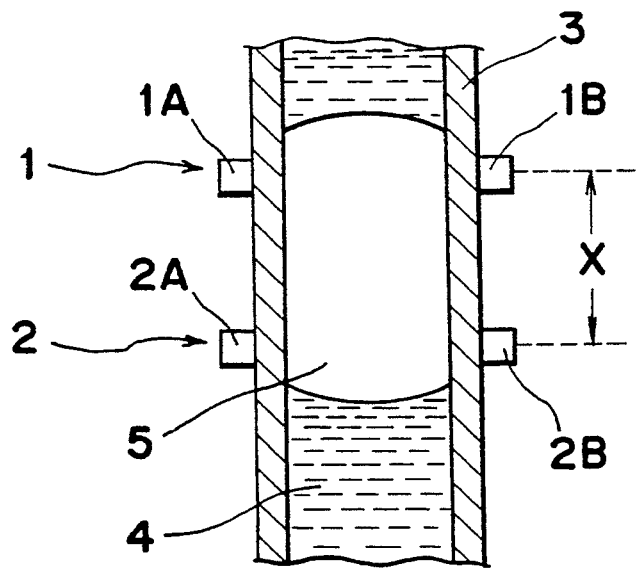
FIG. 1 is a sectional view of a prior art bubble detecting apparatus (already referred to)
Figure 2:
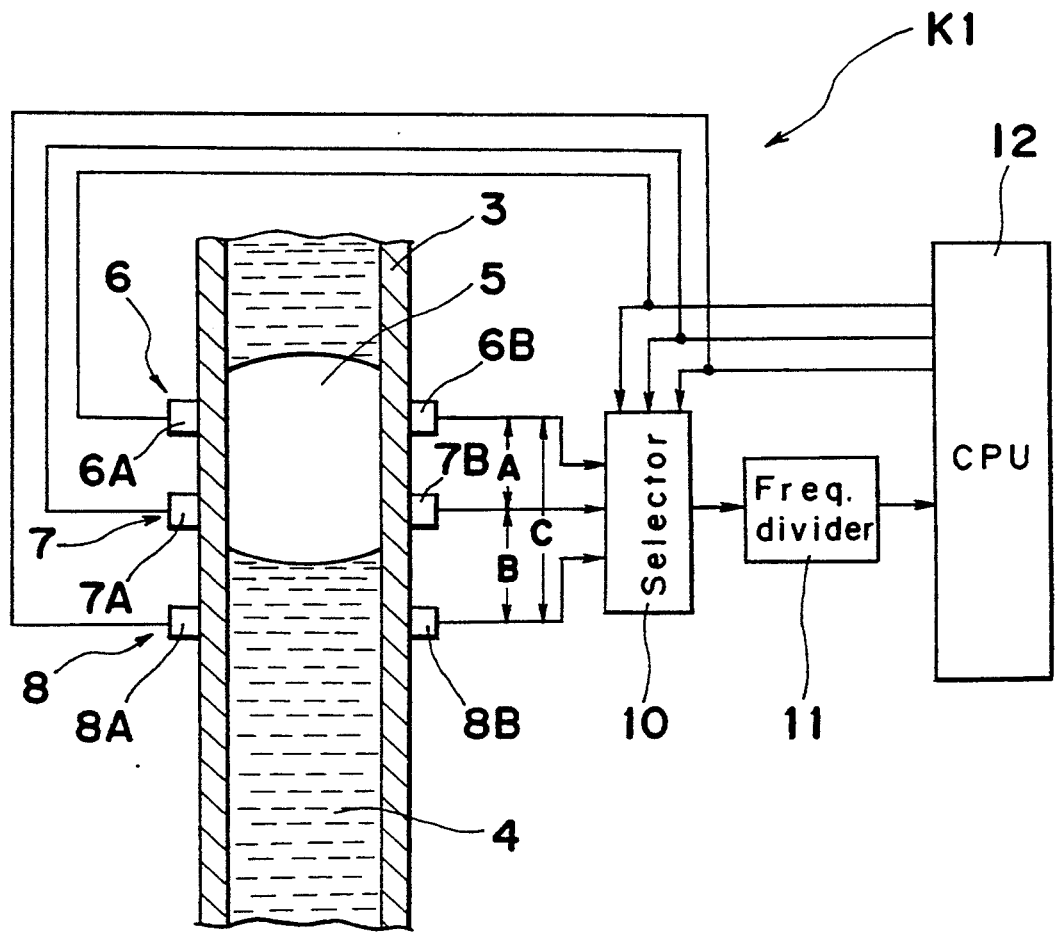
FIG. 2 is a schematic view of a bubble detecting apparatus according to a first embodiment of the present invention.

Referring now to the drawings, there is shown in FIG. 2, a bubble detecting apparatus K1 for an infusion pump, according to a first embodiment of the present invention. The bubble detecting apparatus K1 includes three ultrasonic sensors 6, 7 and 8 for detecting an air bubble 5 produced in or mixed into medicinal liquid 4 in a liquid transport tube 3. The ultrasonic sensor 6 is constituted by an ultrasonic oscillator 6A and a receiver 6B disposed at opposed locations on an outer face of the liquid transport tube 3. Similarly, the ultrasonic sensor 7 is constituted by an ultrasonic oscillator 7A and a receiver 7B, while the ultrasonic sensor 8 is constituted by an ultrasonic oscillator 8A and a receiver 8B. In FIG. 2, characters A, B and C denote a distance between the ultrasonic sensors 6 and 7, a distance between the ultrasonic sensors 7 and 8 and a distance between the ultrasonic sensors 6 and 8, respectively such that the distance B is made larger than the distance A. Desired two of the ultrasonic oscillators 6A, 7A and 8A are selected through a selector 10 by a central processing unit (CPU) 12 formed by a microprocessor. A frequency divider 11 receives only output signals of the two selected ultrasonic oscillators so as to apply to the CPU 12, signals having properly divided frequencies.

Hereinbelow, operation of the bubble detecting apparatus K1 is described. Assuming that the CPU 12 has selected combination of the first and third receivers 6B and 8B through the selector 10, the CPU 12 detects presence of an air bubble 5 in the liquid transport tube 3 when both of the receivers 6B and 8B do not receive ultrasonic waves from the ultrasonic oscillators 6A and 8A, respectively. Therefore, in this case, an air bubble having a size equal to or larger than the distance C can be detected. In case it is necessary to detect the air bubble 5 having a size smaller than the distance C, the air bubble 5 having a size equal to or larger than the distance A or B can be detected by selecting combination of the first and second receiver 6B and 7B or combination of the second and third receivers 7B and 8B. Namely, in the bubble detecting apparatus K1, air bubbles of three kinds of sizes, i.e. air bubbles of sizes not smaller than the distances A, B and C, respectively can be detected.

Figure 3:
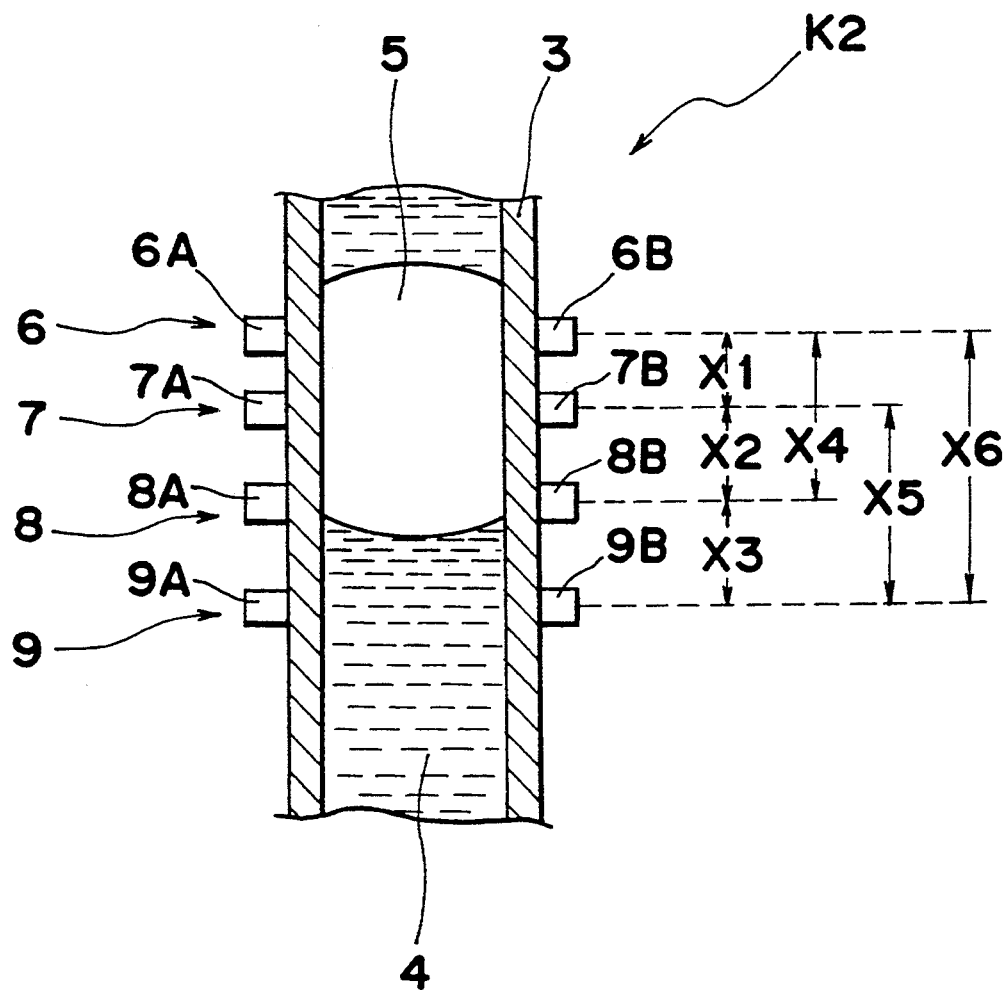
FIG. 3 is a sectional view of a bubble detecting apparatus according to a second embodiment of the present invention.

Referring to FIG. 3, there is shown a bubble detecting apparatus K2 according to a second embodiment of the present invention. In the bubble detecting apparatus K2, four ultrasonic sensors are provided by adding to the ultrasonic sensors 6, 7 and 8 of the bubble detecting apparatus K1, an ultrasonic sensor 9 constituted by an ultrasonic oscillator 9A and a receiver 9B. In FIG. 3, characters X1, X2 and X3 denote a distance between the ultrasonic sensors 6 and 7, a distance between the ultrasonic sensors 7 and 8 and a distance between the ultrasonic sensors 8 and 9, respectively such that the distances X1, X2 and X3 are made gradually larger in this order. Meanwhile, characters X4, X5 and X6 denote a distance between the ultrasonic sensors 6 and 8, a distance between the ultrasonic sensors 7 and 9 and a distance between the ultrasonic sensors 6 and 9, respectively. Thus, the distances X4, X5 and X6 are made gradually larger in this order. In the bubble detecting apparatus K2, air bubbles having six kinds of lengths corresponding to the distances X1 to X6, respectively can be detected by selecting combination of two of the four receivers 6B to 9B.

The bubble detecting apparatus of the present invention can be modified variously. For example, five or more ultrasonic sensors can also be provided. In case five ultrasonic sensors are provided, air bubbles having 10 kinds of lengths can be detected.

As is clear from the foregoing description, in the bubble detecting apparatus for the infusion pump, according to the present invention, three or more ultrasonic sensors are provided along the liquid transport tube at different intervals, respectively. Therefore, sizes of air bubbles to be detected can be selectively set and thus, proper size of air bubbles can be selected in accordance with service temperature of the infusion pump and kinds of medicinal liquid.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. In a bubble detecting apparatus for an infusion pump, including a set of ultrasonic sensors constituted by an ultrasonic oscillator and a receiver provided, respectively, at opposed locations on an outer face of a liquid transport tube for feeding therethrough liquid such as medicinal liquid by a predetermined pumping operation of a pumping mechanism such that air bubbles produced in or mixed into the liquid in said liquid transport tube are detected by said ultrasonic oscillator and said receiver, the improvement comprising:

at least three sets of said ultrasonic sensors which are arranged along said liquid transport tube at different intervals; and further including a selector connected to said receivers of said ultrasonic sensors, a central processing unit connected to said selector and a frequency divider provided between said selector and said central processing unit.

2. The apparatus of claim 1 wherein there are four sets of said ultrasonic sensors.

3. The apparatus of claim 1 wherein there are five sets of said ultrasonic sensors.

4. In a bubble detecting apparatus for an infusion pump, including a set of ultrasonic sensor constituted by an ultrasonic oscillator and a receiver provided, respectively, at opposed locations on an outer face of a liquid transport tube for feeding therethrough liquid such as medicinal liquid by a predetermined pumping operation of a pumping mechanism such that air bubbles produced in or mixed into the liquid in said liquid transport tube are detected by said ultrasonic oscillator and said receiver, the improvement comprising:

at least three sets of said ultrasonic sensors which are arranged along said liquid transport tube at different intervals; and means for selectively activating different sets of said ultrasonic sensors in combination so that air bubbles of varying sizes can be detected.

5. The method of detecting varying size air bubbles in a medicinal liquid passing through a transport tube the air bubbles resulting from operating temperatures of an infusion pump, the method comprising the steps of (a) placing at least three sets of ultrasonic sensor along said tube at different intervals each ultrasonic sensor including an ultrasonic oscillator and receiver;

(b) selectively activating said sets of ultrasonic sensors so that air bubbles of different sizes in the medicinal liquid can be detected.

6. The method of claim 5 wherein the step of placing at different intervals includes providing a second set between the first and third sets and a spacing between the second and third sets is greater than the spacing between the second and first steps so that air bubbles of various sizes can be detected.

* * * * *